(12) United States Patent
Brouillette et al.

(10) Patent No.: US 8,475,775 B1
(45) Date of Patent: Jul. 2, 2013

(54) RETINOIDS AND USE THEREOF

(75) Inventors: Wayne J. Brouillette, Pelham, AL (US); Donald D. Muccio, Hoover, AL (US); Venkatram Reddy Atigadda, Birmingham, AL (US); John M. Ruppert, Birmingham, AL (US); Susan M. Ruppert, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/594,177

(22) Filed: Aug. 24, 2012

(51) Int. Cl.
*C07C 323/59* (2006.01)

(52) U.S. Cl.
USPC ............................. 424/59; 514/562; 562/557

(58) Field of Classification Search
USPC .......................................................... 424/59
See application file for complete search history.

(56) References Cited

U.S. PATENT DOCUMENTS

| | | |
|---|---|---|
| 5,094,783 A | 3/1992 | Muccio et al. |
| 6,172,112 B1 | 1/2001 | Brouillette et al. |
| 2010/0204327 A1 | 8/2010 | Brouillette et al. |
| 2010/0247461 A1 * | 9/2010 | Voronkov et al. ............... 424/59 |

OTHER PUBLICATIONS

Sun S.; Title: Recent Developmetn of Retinoids as therapeutic Agents, Expert Opin. Ther. Patents, 2002, vol. 12, issue 4, published 2002 by Ashley Publications Ltd.*
IPER in PCT/US05/029922.
ISR and Written Opinion in PCT/US05/029922.
Hede, K., "Rexinoids May Be Ready for Prime Time in Prevention, But Challenges Remain," J. Nat'l Cancer Inst., vol. 96 (24), Dec. 15, 2004 USA.
Thacher, S.M.,et al., Receptor Specificity of Retinoid-induced Epidermal Hyperplasia: Effect of RXR-Selective Agonists . . . , JPET vol. 282(2) 1997, at pp. 528-534.
Sun S., Recent Developments of retinoids as therapeutic agents; Expert Opin. Ther. Patents (2002), vol. 12(4); pp. 529-542. Ashley Publications, London (UK).

* cited by examiner

*Primary Examiner* — Janet Epps-Smith
*Assistant Examiner* — Yanzhi Zhang
(74) *Attorney, Agent, or Firm* — Ted Whitlock

(57) ABSTRACT

The present invention provides new retinoid compounds and uses of the compounds in humans and animals for non-neoplastic dermal or inflammatory conditions or disorders.

6 Claims, No Drawings

RETINOIDS AND USE THEREOF

ACKNOWLEDGMENTS

The research leading to this invention was funded in part by the National Institutes of Health, Grant No. 5 P50 CA 89019. The U.S. Government may have certain rights in this invention.

BACKGROUND OF THE INVENTION

Retinoid receptors and other nuclear receptors (that include the steroid, thyroid and vitamin D hormone receptors and other "orphan" receptors without known ligands) are targets for drug development. It is thought that retinoic acid (RA) and synthetic retinoids act as ligand-dependent transcription factors with different members of nuclear retinoid receptors to control gene transcription responsible for cellular proliferation, differentiation, development and cell death. Two classes of nuclear retinoid receptors (RARs and RXRs) have been identified so far, and each has several different subtypes ($\alpha$, $\beta$, $\gamma$). Both (E)-RA and (9Z)-RA bind to RARs and activate transcription mediated by RAR/RXR heterodimers, but (9Z)-RA is the only known natural ligand for the RXRs which mediate transcription by forming homodimers or heterodimers.

Recent advances in chemoprevention have heightened interest in the use of RXR-selective retinoids in several types of solid organ tumors, and major therapeutic successes have been demonstrated with retinoids in certain lymphomas. Bexarotene (a RXR-selective retinoid) is approved for the treatment of Cutaneous T cell Lymphoma.

The wide range of benefits from the uses of these retinoid compounds, including uses in treating, preventing or ameliorating non-neoplastic conditions or disorders, have not been fully identified or explored. Although RAR-selective compounds were known to induce skin hyperplasia, an indicator of retinoid activity in the skin, RXR-selective compounds were previously shown not to be effective inducers of epidermal hyperplasia, considering them silent partners in the RAR-RXR heterodimer with unlikely clinical utility in non-neoplastic skin conditions. See, for example, Thacher, S. M., et al., Receptor Specificity of Retinoid-Induced Epidermal Hyperplasia: Effect of RXR-Selective Agonists and Correlation with Topical Irritation, JPET 282:528-534, 1997. The present invention fulfills a need for new and beneficial uses of retinoid compounds, particularly RXR-selective compounds, for non-neoplastic skin conditions or disorders, as previously not described or realized.

SUMMARY OF THE INVENTION

The present invention concerns certain RXR-selective retinoid compounds, including analogs, derivatives or isomers of these retinoid compounds, and their novel use in methods for treating non-neoplastic dermal conditions or disorders, including dermal inflammatory conditions. The retinoid compounds can be formulated with pharmaceutically acceptable adjuvants, carriers, excipients, or vehicles to provide pharmaceutical compositions useful in the treatment of dermal conditions or disorders. These pharmaceutical compositions can be in the form of oral dosage forms, parenteral (e.g., injectable) dosage forms, or formulated as topical compositions.

Preferred retinoid compounds useful in accordance with the subject invention are designated as UAB30, or analogs, derivatives or isomers of those compounds. The compound, UAB30 and its analogs, as well as a description of how to prepare the compounds, are described in U.S. Pat. No. 6,172,112, which is incorporated herein by reference, in its entirety. Alternative processes for making certain retinoid compounds, including UAB30 or its analogs, as well as compositions comprising those compounds and methods of use, are described in US Patent Application, Publ'n No. 2010/0204327, which is also incorporated herein by reference, in its entirety.

In one embodiment of the present invention, there is provided a method of treating, preventing or ameliorating a dermal condition or disorder such dermatological afflictions associated with excessive skin sebum production (e.g. acne vulgaris) cell differentiation and/or proliferation disorders, (e.g. psoriasis, actinic keratosis, seborrheic dermatitis, warts, hair loss), keratinization disorders (e.g. keratosis, xerosis, iethyosis, lichen, keratoderma, folliculitis), skin pigmentation disorders (e.g. vitiligo, melasma, acnitic lentigines), and/or skin inflammatory disorders (e.g. acne, rosacea, eczema), conditions resulting from photodamage (e.g. such photo induced or chronological skin aging), in an individual in need of such treatment by administering to the individual an effective dose of an RXR-selective retinoid compound, e.g., UAB30, or a composition comprising the compound.

Preferably, the method comprises treating an individual in need of treatment for acne vulgaris, psoriasis, actinic keratosis or skin photo-induced damage. The retinoid compounds can be used in combination with one or more other retinoid compounds, or with one or more other non-retinoid compounds, for the treatment.

Thus, the subject invention concerns a method for treating, preventing or lessening the severity of a non-neoplastic skin condition or disorder in a patient in need thereof, comprising the step of administering to said patient a retinoid compound, or a composition comprising a retinoid compound, having the formula selected from Formula I or Formula II, below:

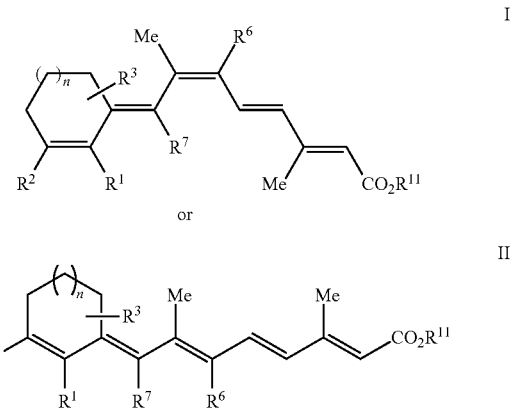

wherein
$R^1$ is H or a $C_1$-$C_5$ or greater branched or straight chain alkyl group;
$R^2$ is H, a $C_1$-$C_{15}$ branched or straight chain alkyl group, a substituted or unsubstituted aryl group, a substituted or unsubstituted aralkyl group, a substituted or unsubstituted cycloalkyl group, or
$R^1$ and $R^2$ collectively form a substituted or unsubstituted fused aryl group;
$R^3$ is one or more groups comprising, independently, H, $CF_3$, a $C_1$-$C_{15}$ branched or straight chain alkyl group, a substituted or unsubstituted aryl group, or a substituted or unsubstituted aralkyl group, a substituted or unsubstituted cycloalkyl group;

$R^6$ and $R^7$ are, independently, H, $CF_3$, a $C_1$-$C_{15}$ branched or straight chain alkyl group, or a substituted or unsubstituted cycloalkyl group;

$R^{11}$ is H, or a $C_1$-$C_{15}$ branched or straight chain alkyl group.

n is from 0 to 3;

wherein one or more carbons in the ring structures of Formula I or II can optionally be replaced with a heteroatom;

or a pharmaceutically acceptable salt or isomer thereof.

More preferably, the method concerns the use of a compound having the formula III, below:

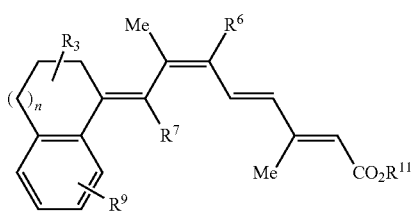

wherein, $R^3$ is one or more groups comprising, independently, H, F, difluoro, $CF_3$, a $C_1$-$C_{15}$ branched or straight chain alkyl group, a substituted or unsubstituted aryl group, or a substituted or unsubstituted aralkyl group, a substituted or unsubstituted cycloalkyl group;

$R^6$ and $R^7$ are, independently, H, $CF_3$, a $C_1$-$C_{15}$ branched or straight chain alkyl group, or a substituted or unsubstituted cycloalkyl group;

$R^9$ is one or more groups comprising, independently, H, F, $CF_3$, a $C_1$-$C_{15}$ branched or straight chain alkyl group, a substituted or unsubstituted aryl group, or a substituted or unsubstituted aralkyl group, or a substituted or unsubstituted cycloalkyl group;

$R^{11}$ is H, or a $C_1$-$C_{15}$ branched or straight chain alkyl group;

n is from 0 to 3;

wherein one or more carbons in the ring structures of Formula I or II can optionally be replaced with a heteroatom;

or a pharmaceutically acceptable salt or isomer thereof.

A most preferred embodiment of the subject method comprises the use of a compound of Formula III is the 9(Z) form having the structure shown as Formula IV, below:

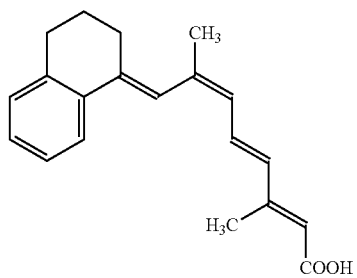

Non-neoplastic skin conditions or disorders treated, prevented or ameliorated by a retinoid compound of the invention include, but are not limited to acne, psoriasis, actinic keratosis, actinic lentigines, seborrheic dermatitis, rosacea, keratosis pillaris, warts, vitiligo, melasma, folliculitis, eczema, icthyosis, lichen, xerosis, keratoderma, hirsutism or hair loss.

The method of the invention can also be useful in treating, preventing or ameliorating a disorder or condition caused by UV damage such as photo-induced skin damage or chronological skin aging. Thus, the method can employ the use of a combination of retinoid compound of the invention with a conventional sun-screening agent.

The subject invention further contemplates pharmaceutical compositions useful for treating, preventing or ameliorating a non-neoplastic dermal condition. Compositions according to the invention comprise, as an active pharmaceutical ingredient (API), at least one retinoid compound as described herein and a pharmaceutically acceptable vehicle or carrier. Preferably, a composition of the invention comprises carriers or vehicles which are pharmaceutically acceptable for oral and/or topical for dermal use or application. More preferably, the composition comprises the compound described herein, designated UAB 30, or an analog, derivative, isomer or salt thereof.

Compositions of the invention can comprise two or more active ingredients, wherein the active ingredients can be two or more retinoid compounds, or can include one or more retinoid compound in combination with a non-retinoid compound. The active ingredients can be administered sequentially or concomitantly.

A composition of the invention comprises an RXR-selective retinoid compound at therapeutically effective doses as can be determined by those of ordinary skill in the art. A retinoid compound of the invention may be provided as a topically applied composition prepared to comprise a concentration of about 0.01 to about 10% of a retinoid compound of the invention as the active pharmaceutical ingredient (API). More preferably, the concentration of retinoid compound in a topically applied composition according to the invention is about 0.025% to about 5%, and most preferably between about 0.1% to about 3% of the composition (w/w in solid and semi-solid dosage forms and w/v in liquid dosage forms).

A retinoid compound of the invention may be provided as an orally administered composition prepared to comprise an amount of about 1 mg to about 600 mg of a retinoid compound of the invention as the active pharmaceutical ingredient (API). More preferably, the amount of retinoid compound in an oral composition according to the invention is about 5 mg to about 300 mg, and most preferably between about 20 mg to about 200 mg of the composition.

Other and further aspects, features, and advantages of the present invention will be apparent from the following description of the presently preferred embodiments of the invention given for the purpose of disclosure.

DETAILED DESCRIPTION OF THE INVENTION

The present invention is directed to RXR-selective retinoid compounds, e.g., UAB30, as disclosed herein, and its novel use in treating dermal conditions or disorders.

In one embodiment of the present invention, there are provided retinoid compounds, e.g., UAB30 and its analogs or isomers, having the general structures selected from the group of Formula I (a 9(Z) isomer) and Formula II (an all-(E) isomer), as shown below:

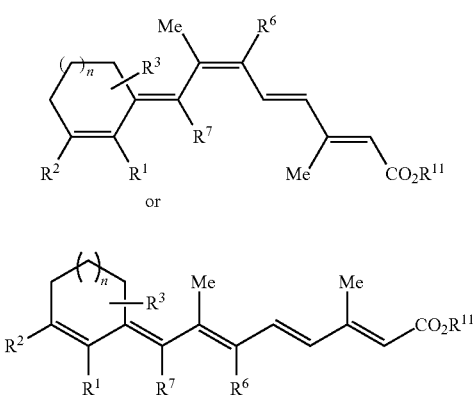

wherein
- $R^1$ is H, $CF_3$, or a C1-C5 or greater branched or straight chain alkyl group;
- $R^2$ is H, $CF_3$, a C1-C15 branched or straight chain alkyl group, a substituted or unsubstituted aryl group, a substituted or unsubstituted aralkyl group, a substituted or unsubstituted cycloalkyl group, or
- $R^1$ and $R^2$ collectively form a substituted or unsubstituted fused aryl group; and
- $R^3$ is one or more groups comprising, independently, H, F, difluoro, $CF_3$, a C1-C15 branched or straight chain alkyl group, a substituted or unsubstituted aryl group, or a substituted or unsubstituted aralkyl group, a substituted or unsubstituted cycloalkyl group;
- $R^6$ and $R^7$ are, independently, H, $CF_3$, a C1-C15 branched or straight chain alkyl group, or a substituted or unsubstituted cycloalkyl group;
- $R^{11}$ is H, or a C1-C15 branched or straight chain alkyl group.
- n is from 0 to 3;

wherein one or more carbons in the ring structures of Formula I or II can optionally be replaced with a heteroatom;
or a pharmaceutically acceptable salt or isomer thereof.

One preferred compound of Formulae I or II above is where $R^1$ is an isopropyl or isopentyl alkane, which includes the compound UAB-111.

More preferably, the method concerns the use of a compound wherein $R^1$ and $R^2$ in Formulae I or II, above, form a fused aryl group wherein the compound has the formula III, below:

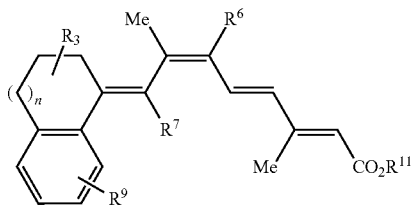

wherein,
- $R^3$ is one or more groups comprising, independently, H, F, difluoro, $CF_3$, a C1-C15 branched or straight chain alkyl group, a substituted or unsubstituted aryl group, or a substituted or unsubstituted aralkyl group, a substituted or unsubstituted cycloalkyl group;
- $R^6$ and $R^7$ are, independently, H, $CF_3$, a C1-C15 branched or straight chain alkyl group, or a substituted or unsubstituted cycloalkyl group;
- $R^9$ is one or more groups comprising, independently, H, F, $CF_3$, a C1-C15 branched or straight chain alkyl group, a substituted or unsubstituted aryl group, or a substituted or unsubstituted aralkyl group, or a substituted or unsubstituted cycloalkyl group;
- $R^{11}$ is H, or a C1-C15 branched or straight chain alkyl group.
- n is from 0 to 3;

wherein one or more carbons in the ring structures of Formula I or II can optionally be replaced with a heteroatom;
or a pharmaceutically acceptable salt or isomer thereof.

A most preferred embodiment is a compound of Formula III, in the 9(Z) form, having the structure shown as Formula IV, below:

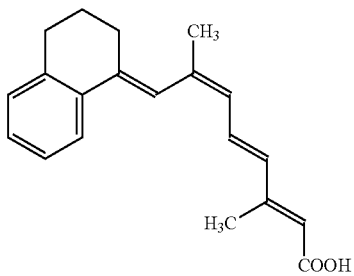

Unless otherwise stated, structures depicted herein are also meant to include all isomeric (e.g., enantiomeric, diastereomeric, and geometric (or conformational) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. In chemical descriptions used herein, "E" may be interchanged synonymously with "trans", and "Z" may be interchanged synonymously with "cis".

In another embodiment, the present invention is directed to a method of treating an individual having a dermal condition or disorder, in which retinoids and its derivatives may be useful. Preferably, the compound is administered at a dosage range of from about 0.001 mg/cm² to about 10 mg/cm² of skin surface, and more preferably between about 0.005 mg/cm² to about 2 mg/cm² of skin surface when applied topically.

Advantageously, compounds used in accordance with the subject invention may also be useful when administered orally. Dosage ranges are preferably from about 0.01 mg/kg to about 300 mg/kg of body weight, and more preferably from about 0.1 mg/kg to about 100 mg/kg of body weight, when administered orally. Compounds of Formula III are especially contemplated as applicable for oral dosing in the treatment of non-neoplastic skin conditions or disorders.

In yet another embodiment of the present invention, there is provided a method of treating an individual having a dermal condition or disorder by administering to the individual a combination of two or more than two retinoid compounds disclosed herein. The combination may further comprise one or more retinoid compound as described herein, and one or more additional active compounds that are not retinoid compounds as disclosed herein.

Representative dermal conditions which can be treated in accordance with the subject invention include, but are not limited to epithelial- or skin-related conditions or disorders. In some embodiments, skin conditions can include dermatological afflictions associated with excessive skin sebum production (e.g. acne vulgaris) cell differentiation and/or proliferation disorders, (e.g. psoriasis, actinic keratosis, seborrheic dermatitis, warts, hair loss) keratinization disorders (e.g. keratosis, xerosis, icthyosis, lichen, keratoderma, folliculitis), skin pigmentation disorders (e.g. vitiligo, melasma, actinic lentigines), and/or skin inflammatory disorders (e.g. acne, rosacea, eczema) and/or conditions resulting from photodamage (e.g. such photo induced or chronological skin aging).

Any of the compounds described herein can be formulated into a pharmaceutical composition. In one aspect, a compound can be combined with at least one pharmaceutically-acceptable carrier to produce a pharmaceutical composition, prepared using techniques known in the art. In one aspect, a composition is prepared by admixing the compound with a pharmaceutically-acceptable carrier. Depending upon the components to be admixed, the components may or may not chemically or physically interact with one another.

Compounds provided herein may be formulated into pharmaceutical compositions that include at least one compound of the present invention, together with one or more pharmaceutically acceptable carriers, including excipients, such as diluents, binders and the like, and can further include additives, such as stabilizing agents, preservatives, solubilizing agents, and buffers, as desired.

Pharmaceutical compositions may include carriers, thickeners, diluents, buffers, preservatives, surface active agents and the like, in addition to the active ingredient. Pharmaceutical compositions may also include more than one active ingredient, such as a retinoid compound according to the invention, and one or more antimicrobial agents, keratolytic agents, benzoyl peroxide, antiinflammatory agents, corticosteroids, or the like. Pharmaceutically-acceptable carriers are known to those skilled in the art. These most typically would be standard carriers for administration to humans, including solutions such as sterile water, saline, and buffered solutions at physiological pH.

The pharmaceutical composition may be formulated for administration in a number of ways depending on whether local or systemic treatment is desired, or depending on the area to be treated. Administration can be topical (applied to the surface of the skin), or as an injectable solution or suspension, preferably for subcutaneous injection. Alternatively, administration can be oral, employing a dosage form such as a tablet or capsule, as would be readily understood by persons of ordinary skill in the art.

In practical use, a provided compound of the present invention can be combined as the active ingredient in an admixture with a pharmaceutical carrier according to conventional pharmaceutical compounding techniques. The carrier used can have different forms depending on the dosage form desired for administration, for example, oral, parenteral, dermal or topical, transdermal, buccal, or the like.

If in an aqueous solution, a provided compound may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate and the like, a 50 mM solution may be employed. In addition to buffering agents, a suitable preservative may be employed, to prevent or limit bacteria and other microbial growth. One such preservative that may be employed is 0.05% benzalkonium chloride.

Preparations for administration include sterile aqueous or non-aqueous solutions, suspensions, and emulsions. Examples of aqueous or non-aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. It will be expected that the actual preferred amounts of active compound in a specified case will vary according to the specific compound being utilized, the particular compositions formulated, the mode of application, and the particular situs and mammal being treated.

In preparing the compositions for oral dosage form, typical pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

For solid administration formulations, any of a variety of thickening, filler, bulking and carrier additives may be employed, such as starches, sugars, fatty acids and the like. Formulation excipients may include polyvinylpyrrolidone, gelatin, hydroxy cellulose, acacia, polyethylene glycol, mannitol, sodium chloride and sodium citrate.

For pharmaceutical formulations, it is also contemplated that any of a variety of measured-release, slow-release or time-release formulations and additives may be employed, so that the dosage may be formulated so as to effect delivery of a provided compound over a period of time, commonly referred to as controlled, delayed, extended, slow, or sustained, release formulations. For example, gelatin, sodium carboxymethylcellulose and/or other cellulosic excipients may be included to provide time-release or slower-release formulations, especially for administration by subcutaneous and intramuscular injection.

The formulation may be such that an application, administration, or injection is required on a daily, weekly, monthly or other periodic basis, depending on the concentration and amount of a provided compound, the biodegradation rate of a polymer used in the formulation, and other factors known to those of skill in the art.

Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999).

The following examples are given for the purpose of illustrating various embodiments of the invention and are not meant to limit the present invention in any fashion.

EXAMPLE 1

Chemistry of Retinoic Acid Analogues $^1$H NMR spectra were obtained at 400.1 MHz (Bruker DRX spectrometer) in $CDCl_3$. NOE experiments were performed on degassed samples using 2D phase-sensitive NOESY experiments with different mixing times (between 250 and 2000 ms). Typically, 1 s mixing times were used with 16 pulses for phase cycling and 2 dummy scans. The data were processed with line broadening of 0.3 Hz in each dimension and zero-filled to yield 512×4096 2D contour plots. The integrated intensities of the negative cross-peaks were determined using standard Bruker NMR software features.

UV/vis spectra were recorded on an AVIV 14DS spectrophotometer in cyclohexane or methanol solutions (Fisher, Spectrograde). IR spectra were recorded using a Nicolet FT IR spectrometer on thin films. HPLC separations were performed on a Gilson HPLC gradient system using 25-ml pump heads and an ISCO V.sup.4 variable wavelength detector. The column employed was a Whatman Partisil 10 M20/50 (500× 22-mm i.d.) with a flow rate of 5 ml/min and monitoring by UV/vis detection at 340 nm. TLC chromatography was performed on pre-coated 250 μm silica gel GF glass plates (Analtech, Inc.; 5×10 cm). Solvents and liquid starting materials were distilled prior to use. Reactions and purifications were conducted with deoxygenated solvents, under inert gas ($N_2$) and subdued lighting. Synthesis methods for retinoid compounds of the subject invention are described in U.S. Pat. No. 6,172,112 and U.S. Pat. Application, Publication No. 2010/0204327, which are incorporated herein by reference in their entirety.

(2E,4E,6E,8E)- and (2Z,4E,6E,8E)-Ethyl 8-(3',4'-Dihydro-1'(2'H)-naphthalen-1'-ylidene-3,7-dimethyl-2,4,6-octatrienoate((all-E)- and (13Z)-5)

This preparation employed a suspension of NaH (0.050 g, 2.1 mmol) in dry THF (1 ml), a solution of triethyl phosphonoseneciaote (0.11 g, 0.40 mmol) in dry THF (1 ml), HMPA (0.048 g, 0.22 mmol), and a solution of (all-E)-4 (0.065 g, 0.31 mmol) in dry THF (1 ml) to give a 2:1 mixture of esters (all-E) and (13)-5 (0.12 g, 78% yield). This mixture was separated by HPLC on silica gel using 1% Et.sub.2 O, 0.5% THF in hexane.

Procedure for the Hydrolysis of Individual Isomers of Ester 5

To a solution of the ester 5 (1 equiv.) in methanol (final concentration 0.061 M) was added an aqueous solution of 2 M KOH (10 equiv.). This solution was heated at reflux, and the reaction progress was monitored by TLC. After 90 min the hot solution was poured into a beaker of ice (40 g) and acidified with 10% HCl until pH2. The mixture was then extracted with $Et_2O$, which was washed with brine, dried ($Na_2SO_4$), and concentrated under reduced pressure to give the product. NMR revealed that the hydrolysis occurred without isomerization. The following acids were synthesized by this method.

(2E,4E,6E,8E)-8-(3',4'-Dihydro-1'(2'H)-naphthalen-1'-ylidene)3,7-dimethyl-2,4,6-octatrienoic acid ((all-E)-UAB30)

This preparation utilized a solution of KOH (0.258 g, 4.61 mmol) in water (2 ml) and a warm solution of ester (all-E)-5 (0.122 g, 0.378 mmol) in methanol (10 ml) to provide acid (all-E)-UAB30 (0.104 g, 93% yield) as a yellow solid: mp 192-197° C. (cyclohexane).

(2E,4E,6E,8E)-8-(3',4'-Dihydro-1'(2'H)-naphthalen-1'-ylidene)3,7-dimethyl-2,4,6-octatrienoic acid ((9Z)-UAB30)

This preparation utilized a solution of KOH (0.15 g, 2.8 mmol) in water (1 ml) and a warm solution of ester (9Z)-5 (0.073 g, 0.23 mmol) in methanol (3 ml) to give acid (9Z)-UAB30 (0.065 g, 98% yield) as a yellow solid: mp 182-185° C. (cyclohexane).

(2E,4E,6E,8E)-8-(3',4'-Dihydro-1'(2'H)-naphthalen-1'-ylidene)3,7-dimethyl-2,4,6-octatrienoic acid ((13Z)-UAB30)

This preparation employed a solution of KOH (0.085 g, 1.50 mmol) in water (1 ml) and a warm solution of ester (13Z)-5 (0.040 g, 0.12 mmol) in methanol (4 ml) to give acid (13Z)-UAB30 (0.034 g, 93% yield) as a yellow solid: mp 180-185° C. (cyclohexane).

EXAMPLE 2

Biology of Retinoic Acid Analogues (Skin Testing)

a. Summary

Compounds UAB30, 4Me-UAB30, UAB111 and Tazarotene were evaluated for possible skin effects (epidermal and dermal thickening as well as skin irritation) following a 14-day topical application in hairless SKH1-E mice. Known RAR-selective retinoids, such as tazarotene, stimulate proliferation of epidermal keratinocytes in human and rodent skin when applied topically. The stimulation the keratinocyte proliferation (reported histologically as epidermal hyperplasia), is believed to be due to increase in the epidermal growth factor receptor activation and is known to be reflective of retinoid effect (Fisher G., Vorhees J., Molecular mechanism of retinoid actions in skin. FASEB J. 1996; 10: 1002-1013). Along with the epidermal hyperplasia, RAR-selective retinoids are associated with significant skin irritation. Previously, RXR-selective retinoids have been reported not to efficiently induce epidermal hyperplasia. Surprisingly, the RXR-selective compound of the subject invention were identified here as exhibiting keratinocyte proliferation effects comparable to a potent RAR-selective retinoid (tazarotene). An additional advantage exhibited by the RXR-selective compounds of the subject invention, compared to tazarotene, was the observation of minimal to no irritation when applied topically.

UAB30, 4Me-UAB30 and UAB111 at 0.1% and 0.3%, tazarotene at 0.1% and vehicle were applied topically on approximately 8 cm2 (2×4 cm) of the dorsal skin (100 μL) and on the right ear (20 μL).

UAB30 topical application resulted in epidermal hyperplasia grading an average of 1.8 and 2 (in a scale of 0=none to 5=marked) for the 0.1% and 0.3% concentrations, respectively. The degree of epidermal hyperplasia induced by UAB30 was comparable to the hyperplasia induced by the potent RAR retinoid tazarotene, 0.1%, that reported an average of 2. 4Me-UBA30 0.1% and 0.3% and UAB111 0.1% and 0.3% treatments caused comparable epidermal hyperplasia ranging from 2.2 to 2.4 in the 5 point scale. Utriculus formation and sebaceous gland hyperplasia, normally present in this mice strain, was also mildly reduced with all the active treatments.

Tazarotene at 0.1% caused severe irritation, measured as erythema, desquamation and skin abrasion in the dorsal skin of all treated mice (Mean skin irritation score=3; scale of 0-4). Vehicle did not cause skin irritation. UAB30 at 0.1% did not cause any irritation whereas the 0.3% concentration was associated with only mild erythema (Mean irritation score=1). 4Me-UAB30 at 0.1% caused mild erythema in 2/5 animals only, however the 0.3% concentration was associated with severe irritation in all mice (Mean irritation score=3.6). UAB111 at 0.1% and 0.3% caused severe irritation (Mean irritation score=3.8) Tazarotene at 0.1%, 4Me-UAB30 at 0.3%, and UAB111 at 0.1% and 0.3% were associated with marked increase in ear Myeloperoxidase (MPO), a marker of neutrophil infiltration, whereas UAB30 at 0.1% and 0.3% and 4Me-UAB30 at 0.1% had no effect in this variable.

It is concluded that UAB30 at 0.1% and 0.3% surprisingly caused epidermal hyperplasia comparable to a potent RAR retinoid but with significantly less irritation when applied topically for 14 days in this hairless mice model.

b. Materials

1. Test Substances and Dosing Pattern

The test compounds were UAB30, 4Me-UAB30 and UAB111. Tazarotene (0.1% cream) was purchased by Ricerca Taiwan Ltd. The three compounds at 0.1% and 0.3%, Tazarotene (0.1% cream) and vehicle (70% ethanol/30% propylene glycol) were each administered topically on the back (100 μL) and on the right ear (20 μL) once daily for two weeks.

The formulations are summarized as follows:

4. Equipment

Animal cage (Techniplast, Italy), Dyer model micrometer gauge (Peacock, Japan), Pipetman (Gilson, France) and Timer (Wisewind, Taiwan).

c. Methods

1. Skin, Topical, Hyperplasia, Irritation Assay.

Female SKH1-E hairless mice (Crl:SKH1-Hrhr) weighing 22±2 g were used. The animals were divided into groups of 5 each. Once a day, 100 μl of vehicle, tazarotene, and test articles were applied on the back with a micropipette and smeared evenly with gloved finger on approximately 8 cm2 (2×4 cm) of the dorsal skin; 20 μl was applied to the right ear. The tested animals were treated for two consecutive weeks. Body weight was monitored twice a week.

2. Retinoid Activity.

Epidermal hyperplasia on the dorsal skin was used as a marker of retinoid activity. For histological evaluation, mice were sacrificed on day 15. The dorsal skin was dissected and stretched to the natural size on the filter. Punch biopsies (ED 8 mm) were obtained, fixed in 10% buffered formalin, and embedded in paraffin. Five micro thick sections were cut, stained with H&E, and a representative section of each biopsy was selected for histological evaluation.

3. Epidermal Measurement.

The thickness of the epidermis and dermis was measured using a microscope with a micrometer in the eyepiece. The details are described in the histopathology report (see d. Histopathology, below).

| Test Compound | Vehicle | Solubility[a] | Color | Light Protection[b] | Temperature | Formulation (mg/mL) |
|---|---|---|---|---|---|---|
| UAB30 | 70% ethanol/ 30% propylene glycol | 5 | Lt. yellow | Y | 4° C. | 1 and 3 |
| 4Me-UAB30 | 70% ethanol/ 30% propylene glycol | 5 | Lt. yellow | Y | 4° C. | 1 and 3 |
| UAB111 | 70% ethanol/ 30% propylene glycol | 5 | Lt. yellow | Y | 4° C. | 1 and 3 |

[a]Based upon visual observation: S: soluble; SS: slight soluble I: insoluble (suspension or ppt.)
[b]Y: kept in tube or vial with brown color, or covered with aluminum foil; N: no protection from light
[c]RT: prepared fresh and stored between 20-25° C.; 4° C.: prepared fresh and stored in the refrigerator or kept on ice.

2. Animals

Female SKH1-E mice weighing 22±2 g, were provided by Charles River, USA. The animals were housed in Individually Ventilated Cages Racks (IVC Racks, 36 Mini Isolator systems) under clean area throughout the experiment. Every 2 or 3 mice were kept in an animal cage (in cm, 26.7 length×20.7 width×14.0 height) and maintained under controlled temperature (20-24° C.) and humidity (50%-80%) with 12-hour light/dark cycles. The animals were given free access to sterilized standard lab chow [MF-18 (Oriental Yeast Co., Ltd. Japan)] and sterile tap water ad libitum. All aspects of this work, i.e., housing, experimentation and disposal of animals, were performed in general accordance with the Guide for the Care and Use of Laboratory Animals (National Academy Press, Washington, D.C., 2011).

3. Chemicals

Absolute ethanol (Merck, Germany), Mouse MPO ELISA kit (HK210, Hycult® biotech, The Netherlands), Propylene glycol (Sigma, USA) and Zorac® (Tazarotene, 1% cream) (Allergan, USA).

4. Skin Irritation.

Erythema, desquamation (skin flaking), and skin lesions/abrasion on dorsal skin were assessed visually in individual animals at the end of a 2-week treatment and scored on a scale of 0 to 4+, with 4+being maximal.

0: Normal
1+: Mild erythema
2+: Moderate erythema
3+: Severe erythema/Desquamation
4+: Lesions/abrasion.

5. Histology.

For histological evaluation, the dorsal skin was dissected and stretched to the natural size on the filter. Punch biopsies (ED 8 mm) were obtained, fixed in 10% buffered formalin, and embedded in paraffin. Five micro thick sections were cut, stained with H&E, and a representative section of each biopsy was selected for histological evaluation. Right ear was harvested on day 15 for measurements of myeloperoxidase activity by mouse MPO ELISA kit, a measure of neutrophil infiltrates.

d. Histopathology

The histopathology findings were as follows:

1) Hyperplasia of the epidermis was noted in all treatment groups except for the vehicle-treated group. Compared to the commercial product 0.1% Tazarotene, UAB30, 4Me-UBA30 and UAB111 treatment resulted in comparable incidence of epidermal hyperplasia.
2) Hyperkeratosis and/or serocellular crust was seen in most of mice treated (3-5 of 5) with 0.1% Tazarotene, UAB111 and 0.3% 4Me-UBA30 but this finding was not reported in the vehicle and 0.3% UAB30 treated mice and only reported in 1 animal of the 0.1% UAB30 group and in 2 mice of the 0.1% 4Me-UBA30 group.

e. Conclusions:

In female SKH1-E hairless mice 14-Day topical application of 0.1% and 0.3% UAB30, 4Me-UBA30 and UAB111 resulted in epidermal hyperplasia comparable to 0.1% tazarotene treatment. UAB30 at 0.1 and 0.3% as well as 4Me-UBA30 at 0.1% caused noticeable less irritation and hyperkeratosis than tazarotene treatment.

Those skilled in the art will readily appreciate that the present invention, or obvious modification thereof, are well adapted to carry out the objects and obtain the advantages mentioned or inherent therein. The present examples along with the methods, procedures, treatments, and compounds or compositions are representative of preferred or exemplary embodiments, and are not intended as limitations to the scope or spirit of the invention.

The invention claimed is:

1. A method for treating or lessening severity of a non-neoplastic skin condition or disorder in a patient having said skin condition or disorder by administering to said patient a compound, or a composition comprising the compound, wherein said compound having a chemical structure as shown in Formula IV:

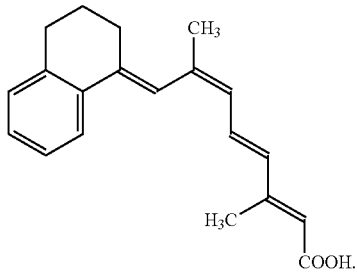

2. The method of claim 1 wherein the skin condition or disorder is selected from dermatological afflictions associated with excessive skin sebum production, and/or cell differentiation and/or proliferation disorders, and/or keratinization disorders and/or skin pigmentation disorders, and/or skin inflammatory disorders.

3. The method of claim 2 wherein the skin condition or disorder is selected from the group consisting of acne vulgaris, psoriasis, actinic keratosis, rosacea, seborrheic dermatitis, actinic lentigines, eczema, warts, keratosis, xerosis, icthyosis, lichen, keratoderma, folliculitis, vitiligo and melasma.

4. The method of claim 2 wherein the skin condition is acne vulgaris.

5. The method of claim 2 wherein the skin condition is psoriasis.

6. The method of claim 2 wherein the skin condition is actinic keratosis.

* * * * *